US010405564B2

United States Patent
Middleton et al.

(10) Patent No.: US 10,405,564 B2
(45) Date of Patent: *Sep. 10, 2019

(54) COMPOSITIONS AND METHODS FOR SMALL CANINES

(71) Applicant: Societe des Produits Nestle S.A., Vevey (CH)

(72) Inventors: Rondo P Middleton, Creve Coeur, MO (US); Christina Petzinger Germain, Imperial, MO (US); Alison Beloshapka, St. Louis, MO (US); James Kaput, Lausanne (CH); Steven S Hannah, Chesterfield, MO (US); Sebastien Lacroix, Quebec (CA); Marie Pier Scott-Boyer, Rovereto (IT); Nikola Djordjevic, Penzberg (DE)

(73) Assignee: Societe des Produits Westle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,313

(22) Filed: Dec. 12, 2017

(65) Prior Publication Data

US 2018/0168193 A1    Jun. 21, 2018

Related U.S. Application Data

(60) Provisional application No. 62/434,563, filed on Dec. 15, 2016.

(51) Int. Cl.
| | |
|---|---|
| *A61P 1/00* | (2006.01) |
| *A61P 3/02* | (2006.01) |
| *A23K 50/40* | (2016.01) |
| *A23K 20/142* | (2016.01) |
| *A23K 20/174* | (2016.01) |
| *A23K 20/179* | (2016.01) |
| *A23K 20/24* | (2016.01) |
| *A23K 20/26* | (2016.01) |
| *A23K 20/28* | (2016.01) |
| *A23K 20/10* | (2016.01) |
| *A23K 20/22* | (2016.01) |
| *A61P 19/08* | (2006.01) |

(52) U.S. Cl.
CPC ............. *A23K 50/40* (2016.05); *A23K 20/10* (2016.05); *A23K 20/142* (2016.05); *A23K 20/174* (2016.05); *A23K 20/179* (2016.05); *A23K 20/22* (2016.05); *A23K 20/24* (2016.05); *A23K 20/26* (2016.05); *A23K 20/28* (2016.05); *A61P 1/00* (2018.01); *A61P 19/08* (2018.01)

(58) Field of Classification Search
CPC ........ A23K 20/26; A23K 20/28; A23K 50/40; A61P 19/08; A61P 1/00
See application file for complete search history.

(56) References Cited

U.S. PATENT DOCUMENTS

| | | | |
|---|---|---|---|
| 6,156,355 A | 12/2000 | Shields | |
| 8,148,325 B2 | 4/2012 | Yamka et al. | |
| 2006/0200320 A1 | 9/2006 | Al-Murrani | |
| 2008/0233428 A1 | 9/2008 | Swenke | |
| 2013/0273196 A1* | 10/2013 | Al-Murrani | A23K 20/111 426/2 |
| 2014/0335180 A1 | 11/2014 | Monginoux et al. | |

FOREIGN PATENT DOCUMENTS

| | | |
|---|---|---|
| EP | 1820407 A1 | 8/2007 |
| EP | 2129237 B1 | 6/2015 |
| WO | 0149130 A1 | 7/2001 |

OTHER PUBLICATIONS

DeBruyne et al. (Nutrition and Diet Therapy. 2007; Cengage Learning 2 pages) (Year: 2007).*
Willihnganz et al. (Basic Pharmacology for Nurses 2014 Elsevier Health Sciences 2 pages). (Year: 2014).*
Jimenez AG. "Physiologcal underpinnings in life-history trade-offs in man's most popular selection experiment: the dog", J Comp Physiol B. May 24, 2016.
Beckmann M, Enot DP, Overy DP, Scott IM, Jones PG, Allaway D, Draper J."Metabolite fingerprinting of urine suggests breed-specific dietary metabolism differences in domestic dogs" Br J Nutr. Apr. 2010;103(8):1127-38. doi: 10.1017/S000711450999300X. Epub Dec. 15, 2009.PMID20003623.
Ko KS, Backus RC, Berg JR, Lame MW, Rogers QR. "Differences in taurine synthesis rate among dogs relate to differences in their maintenance energy requirement", J Nutr. May 2007;137(5):1171-5.PMID:17449577.
International search report, transmittal, and written opinion, PCT/IB2017/057856, dated Apr. 18, 2018.
Nery J et al: "Influence of dietary protein content and source on fecal quality, electrolyte concentrations, and osmolarity and digestibility in dogs differing in body size" Journal of Animal Science, vol. 88, No. 1, 2010, pp. 159-169.

* cited by examiner

*Primary Examiner* — Ernst V Arnold
(74) *Attorney, Agent, or Firm* — Ronald A. Burchett; Aaron Morrow

(57) ABSTRACT

A pet food composition specifically formulated for a small dog can include a combination of specific antioxidants, amino acids, metabolism components, and bone health components to maintain health. Methods of maintaining health and modulating select health parameters are also provided.

15 Claims, No Drawings

US 10,405,564 B2

COMPOSITIONS AND METHODS FOR SMALL CANINES

CROSS REFERENCE TO RELATED APPLICATIONS

This application claims priority to U.S. Provisional Application Ser. No. 62/434,563 filed Dec. 15, 2016, the disclosure of which is incorporated in its entirety herein by this reference.

BACKGROUND

Numerous animal foods are well-known in the art. For canines, foods adapted to a canine's age or size can be found on the market. For example, canine foods intended for puppies, adult, and senior canines are well known and available for purchase at most retail outlets that sell dog foods. Similarly, canine foods intended for overweight canines or canines with particular conditions or diseases are known. U.S. Pat. No. 6,156,355 discloses foods that are designed for specific canine breeds. There are, however, variables other than age, size, and heath that distinguish canines of different breeds and affect their food requirements.

For example, the influence of breed, body weight, age, and gender on energy requirements has been investigated. The results show that some animals having the same body weight have very different energy requirements. Other studies have shown that age-related changes are observed in the metabolism and body composition of papillons, labrador retrievers, and great danes and that these changes affect life expectancy. Studies have shown that some differences exist in terms of body composition and resting metabolic rate and that these differences are independent of body weight. For example, feeding care will differ between a 30 kilogram (kg) labrador and a 30 kg greyhound of the same age and gender and living in the same environmental conditions because their genetic backgrounds are different and these differences result in different metabolisms and body compositions. For example, the greyhound might require more energy per kg of ideal body weight (Kcal per day=150×Kg Body Weight$^{0.75}$) to stay in ideal body condition and the labrador might require less energy (Kcal per day=110×Kg Body Weight$^{0.75}$).

These known foods are useful for a variety of purposes. However, the selection of a particular food for an individual dog or class of dog is often confusing. The consumer must determine the class and type of the dog and select from foods, none of which may be designed for the particular animal that will consume the food. There is, therefore, a need for new methods and compositions that overcome these issues.

SUMMARY

The present disclosure relates generally to pet food compositions; methods of maintaining the health of a small dog; and methods for modulating a health parameter including at least one of bone density, fecal quality, or serum total antioxidant status. Specifically, the present disclosure relates to specific components for small dogs.

The present inventors have discovered that small dogs differ from other dogs based on the results of metabolic profile, blood chemistry, and body composition analysis. A very controlled study was employed to minimize other external factors by using multiple canines all fed the same diet. A validation model was then developed by feeding different levels of the identified compounds (via a dietary change) to a group of canines and measuring changes in the corresponding metabolites.

In one embodiment, a pet food composition for a small dog can comprise at least three antioxidants selected from the group consisting of vitamin E in an amount from about 13 IU to about 1,000 IU per 1,000 kcal of metabolizable energy (ME), vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 mg to about 100 mg per kg of the pet food, proanthocyanidins in an amount of about 1 mg to about 100 mg per kg of the pet food, bioflavonoids in an amount of about 1 mg to about 100 mg per kg of the pet food, and catechins in an amount of about 1 mg to about 100 mg per kg of the pet food; amino acids including phenylalanine, tyrosine, or the combination of phenylalanine and tyrosine, in an amount of about 1.9 g to about 20 g per 1,000 kcal ME; and lysine in an amount of about 1.6 g to about 20 g per 1,000 kcal ME; at least three metabolism components selected from the group consisting of vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, and vitamin B12 in an amount of about 0.007 mg to about 1.5 mg per 1,000 kcal ME; and bone health components including calcium in an amount of about 1.25 g to about 6.25 g per 1,000 kcal ME, phosphorus in an amount of about 1.0 g to about 4.0 g per 1,000 kcal ME, a ratio of calcium to phosphorus ranging from about 1:1 to about 2:1 by weight, magnesium in an amount of about 0.15 g to about 0.55 g per 1,000 kcal ME, and vitamin D in an amount of about 125 IU to about 1,430 IU per 1,000 kcal ME. Additionally, the pet food composition can provide 3,500 to 6,000 kcal ME per kg of the pet food composition on a dry matter basis.

In another embodiment, a method of maintaining the health of a small dog can comprise administering to the small dog a pet food composition as described herein.

In still another embodiment, a method of modulating a health parameter selected from the group consisting of bone density, fecal quality, and serum total antioxidant status, can comprise administering to a small dog a pet food composition as described herein.

Additional features and advantages are described herein and will be apparent from the following Detailed Description.

DETAILED DESCRIPTION

Definitions

As used in this disclosure and the appended claims, the singular forms "a," "an" and "the" include plural referents unless the context clearly dictates otherwise. Thus, for example, reference to "a vitamin" or "the vitamin" includes two or more vitamins. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the food composition unless expressed otherwise. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The term "small dog" or "small canine" refers to canines having a weight of about 16 kg or less.

The term "other dogs" or "other canines" refers to canines having a weight of about 18 kg or more.

The terms "pet food," "pet food product" and "pet food composition" mean a product or composition that is intended for ingestion by a canine that provides at least one nutrient to the animal. Further in this regard, these terms mean that the product or composition is in a form ready for consumption and is not merely an intermediate from which a consumable product or composition is made, although other food compositions can be added in some embodiments, such as a dietary supplement. The term "pet food" means any food composition intended to be consumed by a canine. In an embodiment, the compositions and methods disclosed herein involve a senior dog. Dogs are considered senior in the last 25% of their lives. The life span of a dog depends on its size and/or its breed, but for the present disclosure a senior dog is a dog that is at least 5 years of age (e.g., at least 6 years of age, at least 7 years of age, or at least 8 years of age).

As used herein, "comparable canine" refers to a healthy animal of the same gender, breed, and age as the canine.

As used herein, "metabolite" refers to a compound having biological activity in a companion animal that is an intermediate or product of metabolism, and includes precursors thereof. As used herein, "precursor" refers to any compound that metabolizes to a metabolite during metabolism in a canine. For example, if the specific metabolite is cysteine, "the metabolite" comprises a cysteine precursor (e.g., methionine).

The term "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In one embodiment, the present metabolite or combination of metabolites can be present in an effective amount for modulating a health parameter in a small canine such as bone density, fecal quality, serum total bilirubin, serum gamma-glutamyltransferase, serum total antioxidant status, serum T3, or serum T3/T4, and in one aspect, bone density, serum total antioxidant status, or fecal quality.

The dosages expressed herein are in milligrams per kilogram of body weight per day (mg/kg/day) unless expressed otherwise.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging canines, the canine will continue consuming on a regular basis for the remainder of its life. This can also be referred to as consumption for "extended" periods.

The term "regular basis" or "regular administration" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. The skilled artisan will appreciate that the blood level of a compound or certain metabolites of that compound or which result after the consumption of that compound, may be a useful tool for assessing or determining dosing frequency. For example, for determining feeding amounts for pet food compositions comprising a certain metabolite, the blood concentration of that metabolite, may provide useful information. A frequency, regardless of whether expressly exemplified herein, that allows maintenance of a desired blood level of the measured compound, such as a metabolite, within acceptable ranges can be useful herein. The skilled artisan will appreciate that feeding amounts will be a function of the composition that is being consumed or administered as well as the canine consuming the food, and some food compositions may require more or less frequent administration to maintain a desired blood level of the measured compound (e.g., a metabolite).

The relative terms "improve," "increase," "enhance," "decrease" and the like refer to the effects of the composition disclosed herein (a composition comprising a metabolites) relative to a composition having a lower amount or lacking such metabolites, but otherwise identical.

A "blended" composition merely has at least two components having at least one different characteristic relative to each other. In one aspect, moisture content and water activity can be different in the context of the present disclosure. In this regard, description of a composition as "blended" does not imply that the blended composition has been subjected to processing sometimes referenced as "blending," namely mixing components so that they are indistinguishable from each other, and, in one aspect, such processing is avoided when mixing one component with the other components to form a blended composition (e.g., mixing a dry component with a wet or semi-moist component). Further in this regard, in a blended composition each of the at least two components having at least one different characteristic relative to each other can retain their distinct identity and appearance.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "dietary supplement" means a product that is intended to be ingested in addition to the normal canine diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

The present discussion of embodiments, aspects, examples, etc. are independent in that they can apply to all methods and compositions. For example, a metabolite used in a pet food composition can also be used in the method of modulating or a method of maintaining the health of a canine, and vice versa.

EMBODIMENTS

A pet food composition for a small dog can comprise at least three antioxidants selected from the group consisting of vitamin E, vitamin C, vitamin A, selenium, lycopene, carotenoids, proanthocyanidins, bioflavonoids, and catechins; amino acids including phenylalanine, tyrosine, or the combination of phenylalanine and tyrosine, lysine, and arginine; at least three metabolism components selected from the group consisting of vitamin B1, vitamin B2, vitamin B3, vitamin B5, vitamin B6, vitamin B7, vitamin B9, and vitamin B12; and bone health components including calcium, phosphorus, a ratio of calcium to phosphorus ranging from about 1:1 to about 2:1 by weight, magnesium, and vitamin D. Additionally, the pet food composition can provide about 3,500 to about 6,000 kcal ME per kg of the pet food composition on a dry matter basis.

The present components can be delivered to specifically address the needs of a small dog as presently discovered. In one embodiment, the vitamin E can be present in an amount of about 13 to about 1,000 IU per 1,000 calorie (kcal) of metabolizable energy (ME) of the diet. In more specific embodiments, vitamin E can be present in an amount of about 20 to about 850 IU per 1,000 kcal of ME in the diet, or about 25 to about 700 IU per 1,000 kcal of ME, or about 50 to about 600 IU per 1,000 kcal of ME in the diet.

In one embodiment, vitamin C can be present in an amount of about 0.25 to about 200 IU per 1,000 calorie (kcal) of ME of the diet. In more specific embodiments, vitamin C can be present in an amount of about 20 to about 850 IU per 1,000 kcal of ME in the diet, or about 25 to about 700 IU per 1,000 kcal of ME, or about 50 to about 600 IU per 1,000 kcal of ME in the diet.

In one embodiment, a source of vitamin A can be present in an amount of about 1,300 to about 62,500 IU vitamin A per 1,000 kcal ME in the diet. In more specific embodiments, vitamin can be present in an amount of about 6,000 to about 50,000 IU per 1,000 kcal ME in the diet.

In one embodiment, a source of selenium can be present in an amount of about 0.10 to about 0.5 mg selenium per 1,000 kcal ME in the diet. In other embodiments, selenium can be present in an amount of about 0.11 to about 0.4 mg per 1,000 kcal of ME in the diet, or about 0.12 to about 0.35 mg per 1,000 kcal of ME, or about 0.14 to about 0.28 mg per 1,000 kcal of ME in the diet.

In one embodiment, lycopene can be present in an amount of about 1 to about 100 mg/kg of the diet, or in various alternative embodiments, about 10 to about 90, about 20 to about 80, about 30 to about 70, or about 40 to about 60 mg/kg of the diet.

In one embodiment, carotenoids can be present in an amount of about 1 to about 100 mg/kg of the diet. In more specific embodiments, carotenoids can be present in an amount of about 10 to about 90 mg/kg of the diet, or about 20 to about 80 mg/kg, about 30 to about 70 mg/kg, or about 40 to about 60 mg/kg of the diet.

The diets also contains other ingredients, e.g., grape seed extract or other plants, which provides proanthocyanidins, bioflavonoids, and catechins. In various embodiments, suitable amounts of proanthocyanidins, bioflavonoids, and catechins that can be included in the diet are about 1 to about 500, about 1 to about 250, about 1 to about 100, or about 1 to about 50 mg/kg.

In one embodiment, a source of phenylalanine and/or tyrosine can be present in an amount of about 1.9 to about 20 g per 1,000 kcal ME in the diet. In other embodiments, phenylalanine and/or tyrosine can be present in an amount of about 2.3 to about 17 g per 1,000 kcal of ME in the diet, or about 3 to about 15 g per 1,000 kcal of ME, or about 4 to about 12 g per 1,000 kcal of ME in the diet.

In one embodiment, a source of lysine can be present in an amount of about 1.6 to about 20 g per 1,000 kcal ME in the diet. In other embodiments, lysine can be present in an amount of about 1.9 to about 14 g per 1,000 kcal of ME in the diet, or about 2.3 to about 10 g per 1,000 kcal of ME, or about 3 to about 6.5 g per 1,000 kcal of ME in the diet.

In one embodiment, a source of arginine can be present in an amount of about 1.28 to about 25 g per 1,000 kcal ME in the diet. In other embodiments, lysine can be present in an amount of about 1.28 to about 18 g per 1,000 kcal of ME in the diet, or about 2.3 to about 12 g per 1,000 kcal of ME, or about 1.28 to about 6.5 g per 1,000 kcal of ME in the diet.

In one embodiment, a source of vitamin B1 (thiamine) can be present in an amount of about 0.56 to about 150.0 mg per 1,000 kcal ME in the diet. In other embodiments, vitamin B1 can be present in an amount of about 1.0 to about 120.0 mg per 1,000 kcal of ME in the diet, or about 2.0 to about 80.0 mg per 1,000 kcal of ME, or about 3.0 to about 46.5 mg per 1,000 kcal of ME in the diet.

In one embodiment, a source of vitamin B2 (riboflavin) can be present in an amount of about 1.3 to about 50.0 mg per 1,000 kcal ME in the diet. In other embodiments, vitamin B2 can be present in an amount of about 1.3 to about 40 mg per 1,000 kcal of ME in the diet, or about 1.4 to about 25 mg per 1,000 kcal of ME, or about 1.5 to about 10.0 mg per 1,000 kcal of ME in the diet.

In one embodiment, a source of vitamin B3 (niacin, nicotinic acid) can be present in an amount of about 3.4 to about 500.0 mg per 1,000 kcal ME in the diet. In other embodiments, vitamin B3 can be present in an amount of about 5.0 to about 400.0 mg per 1,000 kcal of ME in the diet, or about 10.0 to about 350 mg per 1,000 kcal of ME, or about 20.0 to about 250.0 mg per 1,000 kcal of ME in the diet.

In one embodiment, a source of vitamin B5 (pantothenic acid, pantothenate) can be present in an amount of about 3.0 to about 300 mg per 1,000 kcal ME in the diet. In other embodiments, vitamin B5 can be present in an amount of about 3.5 to about 200 mg per 1,000 kcal of ME in the diet, or about 4.0 to about 150 mg per 1,000 kcal of ME, or about 5.5 to about 80 mg per 1,000 kcal of ME in the diet.

In one embodiment, a source of vitamin B6 (pyridoxine, pyridoxal, pyridoxamine) can be present in an amount of about 0.38 to about 200.0 mg per 1,000 kcal ME in the diet. In other embodiments, vitamin B6 can be present in an amount of about 0.75 to about 125 mg per 1,000 kcal of ME in the diet, or about 1.5 to about 90.0 mg per 1,000 kcal of ME, or about 3.0 to about 35.0 mg per 1,000 kcal of ME in the diet.

In one embodiment, a source of vitamin B7 (biotin) can be present in an amount of about 0.01 to about 10.0 mg per 1,000 kcal ME in the diet. In other embodiments, vitamin B7 can be present in an amount of about 0.015 to about 6.0 mg per 1,000 kcal of ME in the diet, or about 0.02 to about 2.0 mg per 1,000 kcal of ME, or about 0.035 to about 0.8 mg per 1,000 kcal of ME in the diet.

In one embodiment, a source of vitamin B9 (folic acid, folate) can be present in an amount of about 0.054 to about 40.0 mg per 1,000 kcal ME in the diet. In other embodiments, vitamin B9 can be present in an amount of about 0.1 to about 25.0 mg per 1,000 kcal of ME in the diet, or about 0.2 to about 15.0 mg per 1,000 kcal of ME, or about 0.30 to about 4.5 mg per 1,000 kcal of ME in the diet.

In one embodiment, a source of vitamin B12 (cobalamin, cyclocobalamin, methylcobalamin) can be present in an amount of about 0.007 to about 1.5 mg per 1,000 kcal ME in the diet. In other embodiments, vitamin B12 can be present in an amount of about 0.01 to about 1.0 mg per 1,000 kcal of ME in the diet, or about 0.012 to about 0.6 mg per 1,000 kcal of ME, or about 0.015 to about 0.3 mg per 1,000 kcal of ME in the diet.

In one embodiment, a source of calcium can be present in an amount of about 1.25 to about 6.25 g per 1,000 kcal ME in the diet. In other embodiments, calcium can be present in an amount of about 1.6 to about 5.9 g per 1,000 kcal of ME in the diet, or about 2.0 to about 5.0 g per 1,000 kcal of ME, or about 2.5 to about 4.5 g per 1,000 kcal of ME in the diet.

In one embodiment, a source of phosphorus can be present in an amount of about 1.0 to about 4.0 g per 1,000 kcal ME in the diet. In other embodiments, phosphorus can be present in an amount of about 1.5 to about 3.8 g per 1,000 kcal of ME in the diet, or about 2.0 to about 3.6 g per 1,000 kcal of ME, or about 2.3 to about 3.4 g per 1,000 kcal of ME in the diet.

In one embodiment, a ratio of calcium to phosphorus can be present in an amount of about 1:1 to about 2:1 in the diet by weight. In other embodiments, a ratio of calcium to phosphorus can be present in an amount of about 1:1 to about 1.8:1 by weight, or about 1:1 to about 1.6:1 by weight in the diet.

In one embodiment, a source of magnesium can be present in an amount of about 0.15 to about 0.55 g per 1,000 kcal ME in the diet. In other embodiments, magnesium can be present in an amount of about 0.16 to about 0.45 or about 0.17 to about 0.35 g per 1,000 kcal of ME in the diet.

In one embodiment, a source of vitamin D can be present in an amount of about 125 to about 1,430 IU per 1,000 kcal ME in the diet. In more specific embodiments, vitamin D can be present in an amount of about 225 to about 1,300 IU per 1,000 kcal ME in the diet, or about 275 to about 1,200, or about 350 to about 1,100 IU per 1,000 kcal ME in the diet.

Generally, the pet food composition includes at least three antioxidants. In one embodiment, the pet food composition can comprise at least 4 antioxidants. In another embodiment, the pet food composition can comprise at least 5 antioxidants. In still another embodiment, the pet food composition can comprise at least 6 antioxidants. In yet another embodiment, the pet food composition can comprises each one of vitamin E, vitamin C, vitamin A, selenium, lycopene, carotenoids, proanthocyanidins, bioflavonoids, and catechins. In one specific aspect, the pet food composition can include each one of vitamin E in an amount from 13 about IU to about 1,000 IU per 1,000 kcal ME, vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 to about 100 mg per kg of the pet food, proanthocyanidins in an amount of about 1 mg to about 100 mg per kg of the pet food, bioflavonoids in an amount of about 1 mg to about 100 mg per kg of the pet food, catechins in an amount of about 1 mg to about 100 mg per kg of the pet food.

Generally, the pet food composition comprises B vitamins that are essential to the health of the canine. In one embodiment, the pet food composition can comprise vitamin B1, vitamin B2, vitamin B3, vitamin B5, vitamin B6, vitamin B7, vitamin B9, and vitamin B12. In one specific aspect, the pet food composition can comprise each one of vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, and vitamin B12 in an amount of about 0.007 mg to about 1.5 mg per 1,000 kcal ME.

Generally, the pet food composition comprises essential amino acids for maintaining health. In one embodiment, the pet food composition comprises phenylalanine, tyrosine, or the combination of phenylalanine and tyrosine; and lysine. In one specific aspect, the pet food composition comprises amino acids including phenylalanine, tyrosine, or the combination of phenylalanine and tyrosine in an amount of 1.9 g to 20 g per 1,000 kcal ME; and lysine in an amount of 1.6 g to 20 g per 1,000 kcal ME.

Generally, the pet food composition comprises essential bone health components for maintaining bone health. In one embodiment, the pet food composition comprises calcium, phosphorous, magnesium, and vitamin D. Additionally, the pet food composition can contain a ratio of calcium to phosphorous specific for small dogs. In one specific aspect, the pet food composition comprises bone health components including calcium in an amount of about 1.25 g to about 6.25 g per 1,000 kcal ME, phosphorus in an amount of about 1.0 g to about 4.0 g per 1,000 kcal ME, a ratio of calcium to phosphorus ranging from about 1:1 to about 2:1 by weight, magnesium in an amount of about 0.15 g to about 0.55 g per 1,000 kcal ME, and vitamin D in an amount of about 125 IU to about 1,430 IU per 1,000 kcal ME.

Generally, the pet food composition is formulated for small dogs. As such, in one embodiment, the pet food composition provides 3,000 to 6,000 kcal ME per kg of the pet food composition on a dry matter basis.

Additionally, the pet food compositions can comprise metabolites that have been shown as significant for small dogs. In one embodiment, the pet food can include at least three metabolites for modulating antioxidant concentration in the small dog, the metabolites selected from the group consisting of 5-oxoproline, gamma-glutamylphenylalanine, urate, gamma-glutamylisoleucine, gamma-glutamylleucine, gamma-glutamylvaline, gamma-glutamyltyrosine, xylonate, arabonate, gamma-glutamylmethionine, gulono-1,4-lactone, bilirubin (E,E), cysteine-glutathione disulfide, and threonate. In one aspect, the pet food composition can include at least 3 metabolites for modulating amino acid concentration in the small dog, the metabolites selected from the group consisting of phenylalanine, p-cresol sulfate, phenol sulfate, glutamine, tyrosine, arginine, and lysine.

In one specific aspect, the pet food composition can comprise vitamin E in an amount from about 50 IU to about 600 IU per 1,000 kcal ME, vitamin C in an amount from about 50 IU to about 600 IU per 1,000 kcal ME, vitamin A in an amount of about 6,000 IU to about 50,000 IU per 1,000 kcal ME, selenium in an amount of about 0.14 mg to about 0.28 mg per 1,000 kcal ME, lycopene in an amount of about 40 mg to about 60 mg per kg of the pet food, carotenoids in an amount of about 40 mg to about 60 mg per kg of the pet food, proanthocyanidins in an amount of about 1 mg to about 50 mg per kg of the pet food, bioflavonoids in an amount of about 1 mg to about 50 mg per kg of the pet food, and catechins in an amount of about 1 mg to about 50 mg per kg of the pet food; phenylalanine, tyrosine, or combination of phenylalanine and tyrosine in an amount of about 4 g to about 12 g per 1,000 kcal ME; and lysine in an amount of about 3 g to about 6.5 g per 1,000 kcal ME; vitamin B1 in an amount of about 3.0 mg to about 46.5 mg per 1,000 kcal ME, vitamin B2 in an amount of about 1.5 mg to about 10.0 mg per 1,000 kcal ME, vitamin B3 in an amount of about 20.0 mg to about 250.0 mg per 1,000 kcal ME, vitamin B5 in an amount of about 5.5 mg to about 80.0 mg per 1,000 kcal ME, vitamin B6 in an amount of about 3.0 mg to about 35.0 mg per 1,000 kcal ME, vitamin B7 in an amount of about 0.035 mg to about 0.8 mg per 1,000 kcal ME, vitamin B9 in an amount of about 0.30 mg to about 4.5 mg per 1,000 kcal ME, and vitamin B12 in an amount of about 0.015 mg to about 0.3 mg per 1,000 kcal ME; and calcium in an amount of about 2.5 g to about 4.5 g per 1,000 kcal ME, phosphorus in an amount of about 2.3 g to about 3.4 g per 1,000 kcal ME, ratio of calcium to phosphorus ranging from about 1:1 to about 1.6:1 by weight, magnesium in an amount of about 0.17 g to about 0.35 g per 1,000 kcal ME, and vitamin D in an amount of about 350 IU to about 1,100 IU per 1,000 kcal ME.

In one embodiment, a method of maintaining the health of a small dog can comprise administering to the small dog a pet food composition as described herein. In one aspect, the administering can be a regular administration.

In another embodiment, a method of modulating a health parameter selected from the group consisting of bone density, fecal quality, and serum total antioxidant status, can comprise administering to a small dog a pet food composition as described herein.

Generally, the method of modulating can provide an increase or decrease in a health parameter (such as bone density or serum total antioxidant status) after administration of the pet food composition. In one embodiment, the health parameter can be increased or decreased by at least 5%. In other aspects, the health parameter can be increased or decreased by 10%, 15%, 20%, 25%, 30%, 35%, 40%, 45%, or even 50%, or higher. In one specific aspect, the health parameter can be increased. In another specific aspect, the health parameter can be decreased. In another aspect, fecal quality can be improved.

In each of these compositions and methods, the pet food composition can be a wet food, a semi-moist food or a dry food. In an embodiment, the pet food composition is one or more components of a blended composition. In some embodiments, the pet food composition is a kibble, and in some embodiments, the pet food composition is a meat analog. Additionally, in another embodiment, the present composition can be a dietary supplement comprising the components described herein.

Such pet food compositions can be administered to the canine in amounts ranging from about 3 g of pet food per 1 lb body weight to about 16 g of pet food per 1 lb body weight of the canine. Additionally, the metabolites can be present in amounts from about 0.01 weight % to about 10 weight % of the food composition. In one aspect, the metabolites can be present in concentrations of about 0.01 to about 1,000 mg/kg of food. In another aspect, the metabolites can be present in concentrations from about 1 IU to about 500,000 IU per kilogram of food. In one embodiment, the pet food composition can be administered to the canine in amounts sufficient to maintain the health and/or body weight of the animal.

As noted above and detailed later in this application, the present inventors identified metabolite compounds which correlate to small dogs. Thus, the pet food composition can comprise one of these compounds.

As another non-limiting example, the metabolite can be selected from the group consisting of creatine, creatinine, 5-oxoproline, gamma-glutamylphenylalanine, X-18487, hydroxyproline, phenylalanine, X-14625, X-17381, p-cresol sulfate, X-11334, urate, X-13731, gamma-glutamylisoleucine, gamma-glutamylleucine, gamma-glutamylvaline, pseudouridine, phenol sulfate, X-12668, C-glycosyltryptophan, myo-inositol, 17-methyistearate, X-14314, glutamine, X-12010, glycolate (hydroxyacetate), gamma-glutamyltyrosine, X-12822, xylonate, prolylhydroxyproline, mannitol, hydroquinone sulfate, ethanolamine, 4-ethylphenyl sulfate, arabonate, N6-carbamoylthreonyladenosine, pantothenate (Vitamin B5), pyroglutamine, gamma-glutamylmethionine, X-16940, citrulline, tyrosine, gulono-1,4-lactone, methylpalmitate (15 or 2), X-16394, xylitol, arginine, 2'-deoxycytidine, 2'-O-methylguanosine, ophthalmate, homocitrulline, 5-methylcytidine, N-formylmethionine, bilirubin (E,E), X-17299, X-18156, palmitoyl sphingomyelin, X-16945, cysteine-glutathione disulfide, 4-vinylphenol sulfate, erythritol, dihomolinolenate (20:3n3 or 3n6), anthranilate, lysine, threitol, threonate, and mixtures thereof.

As yet another non-limiting example, the metabolite can be selected from the group consisting of creatine, creatinine, 5-oxoproline, gamma-glutamylphenylalanine, hydroxyproline, phenylalanine, p-cresol sulfate, urate, gamma-glutamylisoleucine, gamma-glutamylleucine, gamma-glutamylvaline, pseudouridine, phenol sulfate, C-glycosyltryptophan, myo-inositol, 17-methylstearate, glutamine, glycolate (hydroxyacetate), gamma-glutamyltyrosine, xylonate, prolyl-hydroxyproline, mannitol, hydroquinone sulfate, ethanolamine, 4-ethylphenyl sulfate, arabonate, N6-carbamoylthreonyladenosine, pantothenate (Vitamin B5), pyroglutamine, gamma-glutamylmethionine, citrulline, tyrosine, gulono-1,4-lactone, methylpalmitate (15 or 2), xylitol, arginine, 2'-deoxycytidine, 2'-O-methylguanosine, ophthalmate, homocitrulline, 5-methylcytidine, N-formyl-methionine, bilirubin (E,E), palmitoyl sphingomyelin, cysteine-glutathione disulfide, 4-vinylphenol sulfate, erythritol, dihomolinolenate (20:3n3 or 3n6), anthranilate, lysine, threitol, threonate, and mixtures thereof.

As noted above, ingredients comprising the metabolite (e.g., a precursor of the metabolite) and optionally amounts of the metabolite in the ingredient can be identified by analysis of the ingredient, for example using a separation technique, such as gas chromatography or liquid chromatography, and then mass spectrometry.

The pet food compositions disclosed herein can be any food formulated for consumption by a canine. In an embodiment, the pet food composition provides complete nutrition as defined by the Association of American Feed Control Officials (AAFCO) for a canine.

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

The pet food compositions disclosed herein can comprise vegetable oil, a flavorant, a colorant and water. Suitable vegetable oils include soybean oil, corn oil, cottonseed oil, sunflower oil, canola oil, peanut oil, safflower oil, and the like. Examples of suitable flavorants include yeast, tallow, rendered animal meals (e.g., poultry, beef, lamb, pork), flavor extracts or blends (e.g., grilled beef), animal digests, and the like. Suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as other grains and/or other starches additionally or alternatively to flour, amino acids, fibers, sugars, animal oils, aromas, other oils additionally or alternatively to vegetable oil, humectants, preservatives, polyols, salts, oral care ingredients, antioxidants, vitamins, minerals, probiotic microorganisms, bioactive molecules or combinations thereof.

Suitable starches include a grain such as corn, rice, wheat, barley, oats, soy and the like, and mixtures of these grains, and can be included at least partially in any flour. Suitable humectants include salt, sugars, propylene glycol and polyhydric glycols such as glycerin and sorbitol, and the like. Suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Examples of suitable antioxidants include butylated hydroxyanisole ("BHA") and butylated hydroxytoluene ("BHT"), vitamin E (tocopherols), and the like.

Non-limiting examples of vitamins that can be used include Vitamins A, B-complex (such as B-1, B-2, B-6 and B-12), C, D, E and K, niacin and acid vitamins such as pantothenic acid and folic acid and biotin. Non-limiting examples of suitable minerals include calcium, iron, zinc, magnesium, iodine, copper, phosphorus, manganese, potassium, chromium, molybdenum, selenium, nickel, tin, silicon, vanadium, boron and the like.

Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like.

EXAMPLES

The following non-limiting examples are illustrative of embodiments of the present disclosure.

Example 1—Small Dog Study 83 canines were all fed the same kibble diet for 5 weeks. Small dogs (34) weighed an average of 9.3 kg (6.1-15.6 kg). Other dogs (49) weighed an average of 31.5 kg (18.4-54.4 kg). Plasma samples were taken after overnight fasting using EDTA vacutainer tubes during the fifth week of feeding of each diet. After centrifugation, plasma was aliquoted into cryovials and frozen at −80° C.

TABLE 1

| Moisture Basis | Moisture % | DM % | Protein % | Fat % | Ash % | Fiber % | CHO % | GE kcal/g |
|---|---|---|---|---|---|---|---|---|
| Diet A | | | | | | | | |
| As-Is | 8.1 | 91.9 | 22.7 | 13.3 | 6.1 | 2.0 | 47.9 | 4.5 |
| Dry matter | 0 | 100 | 24.7 | 14.5 | 6.6 | 2.1 | 52.1 | 4.9 |
| Diet B | | | | | | | | |
| As-Is | 76 | 24 | 9.1 | 10.5 | 1.8 | 0 | 2.6 | 1.7 |
| Dry Matter | 0 | 100 | 38 | 43.7 | 7.5 | 0 | 10.8 | 6.9 |

Metabolomic analysis was carried out using the following methods by Metabolon Inc. Samples were extracted and split into equal parts for analysis on GC/MS and LC/MS/MS platforms. Proprietary software was used to match ions to an in-house library of standards for metabolite identification and for metabolite quantitation by peak area integration by Metabolon Inc. Mass and retention index are provided in the following tables such that each metabolite can be uniquely identified and individually distinguished.

At the time of analysis, samples were thawed and extracts prepared to remove protein, dislodge small molecules bound to protein or physically trapped in the precipitated protein matrix, and recover a wide range of chemically diverse metabolites. A separate aliquot of each experimental plasma sample was taken then pooled for the creation of "Client Matrix" (CMTRX) samples. These CMTRX samples were injected throughout the platform run and served as technical replicates, allowing variability in the quantitation of all consistently detected biochemicals to be determined and overall process variability and platform performance to be monitored. Extracts of all experimental and CMTRX samples were split for analysis on the GC/MS and LC/MS/MS platforms.

The CMTRX technical replicate samples were treated independently throughout the process as if they were client study samples. All process samples (CMTRX and Grob test mixtures of organic components used to assess GC column performance, process blanks, etc.) were spaced evenly among the injections for each day and all client samples were randomly distributed throughout each day's run. Data were collected over multiple platform run days and thus 'block normalized' by calculating the median values for each run-day block for each individual compound. This normalization minimizes any inter-day instrument gain or drift, but does not interfere with intra-day sample variability. Missing values (if any) were assumed to be below the level of detection for that biochemical with the instrumentation used and were imputed with the observed minimum for that particular biochemical.

A number of internal standards were added to each experimental and process standard sample just prior to injection into the mass spectrometers. A measure of the platform variability (7%) was determined by calculating the median relative standard deviation (RSD) for these internal standards. Because these standards are added to the samples immediately prior to injection into the instrument, this value reflects instrument variation. In addition, the median relative standard deviation (RSD) for the biochemicals that were consistently measured in the CMTRX represents the total variability within the process for the actual experimental samples and the variability in quantitation of the endogenous metabolites within these samples (12%). Results for the CMTRX and internal standards indicated that the platform produced data that met process specifications.

589 total metabolites were detected in plasma. This total corresponds to many biochemicals (401) that matched a named structure in the reference library (named compounds). The remaining biochemicals (188) represent distinct chemical entities (that is, they represent a single molecule of discrete molecular formula and structure), but they do not currently match a named biochemical in the reference library (unnamed/unknown compounds).

Clinical measures were carried out with all dogs except for bone density (DEXA), T3 and T4 which were carried out with all small dogs (34) and 35 other dogs weighing an average of 26.4 kg (18.4-32.1 kg). Serum creatinine, creatine kinase, potassium, total bilirubin, total antioxidant status (TAS), aspartate transaminase (AST), gamma-glutamyl-transferase (GGT), total T3, total T4 were measured using the Cobas® c311 or e411 clinical chemistry analyzer, according to manufacturer's directions. Protein digestibility was determined based on amount of protein in food consumed, amount in feces and corrected for microbial nitrogen. Bone density was measured using dual-energy x-ray absorptiometry (DEXA) according to manufacturer's directions.

Benjamini-Hochberg adjusted P values were determined for all clinical measures except for T3/T4 ratio where standard P-values were determined and protein digestibility where Mann Whitney was performed.

Metabolite correlations between small dog and other dogs are shown in Table 2. Clinical measures between small dog and other dogs are shown in Table 3.

TABLE 2

Specific Metabolite ratios between small dogs and other dogs. Correlations with a P value < 0.05 are reported.

| ID | Ratio (Small/Others) | P-Value | Retention Index | Mass |
|---|---|---|---|---|
| creatine | 2.81 | 7.35E−08 | 758 | 132.1 |
| creatinine | 0.78 | 2.47E−07 | 730 | 114.1 |
| 5-oxoproline | 0.78 | 3.28E−07 | 744 | 128.2 |
| gamma-glutamylphenylalanine | 0.71 | 3.66E−06 | 2846 | 295.1 |
| X - 18487 | 0.48 | 5.41E−06 | 1269.6 | 273.1 |
| hydroxyproline | 0.72 | 7.97E−05 | 705 | 132.1 |
| phenylalanine | 0.84 | 7.97E−05 | 2056 | 166.1 |
| X - 14625 | 0.82 | 7.97E−05 | 742 | 308.1 |
| X - 17381 | 2.94 | 7.97E−05 | 4159.8 | 293.1 |
| p-cresol sulfate | 1.48 | 1.05E−04 | 2896 | 187.1 |
| X - 11334 | 0.47 | 1.19E−04 | 982 | 259.1 |
| urate | 0.72 | 1.58E−04 | 1928 | 441.2 |
| X - 13731 | 1.92 | 3.57E−04 | 1902 | 235 |
| gamma-glutamylisoleucine | 0.78 | 4.15E−04 | 2644 | 261.2 |
| gamma-glutamylleucine | 0.76 | 4.15E−04 | 2744 | 261.2 |
| gamma-glutamylvaline | 0.77 | 4.64E−04 | 2040 | 247.2 |
| pseudouridine | 0.89 | 4.96E−04 | 1104 | 243.1 |
| phenol sulfate | 1.74 | 6.12E−04 | 2150 | 173.1 |
| X - 12668 | 1.72 | 6.76E−04 | 2318 | 246.1 |
| C-glycosyltryptophan | 0.79 | 9.31E−04 | 1912 | 367.1 |
| myo-inositol | 0.79 | 0.001 | 1924.9 | 217 |
| 17-methylstearate | 1.42 | 0.001 | 5987 | 297.4 |
| X - 14314 | 0.79 | 0.001 | 2302 | 241.1 |
| glutamine | 0.89 | 0.002 | 684 | 147.2 |
| X - 12010 | 0.72 | 0.002 | 1707 | 203.1 |
| glycolate (hydroxyacetate) | 0.87 | 0.002 | 1119 | 177 |
| gamma-glutamyltyrosine | 0.75 | 0.002 | 2073 | 311.2 |
| X - 12822 | 0.62 | 0.004 | 2786 | 389.1 |
| xylonate | 0.58 | 0.004 | 1722 | 292 |
| prolylhydroxyproline | 0.19 | 0.005 | 960 | 229.2 |
| mannitol | 0.33 | 0.005 | 1839 | 319.1 |
| hydroquinone sulfate | 1.57 | 0.005 | 1383 | 189 |
| ethanolamine | 0.61 | 0.005 | 1304 | 174.1 |
| 4-ethylphenyl sulfate | 1.50 | 0.006 | 3570 | 201.1 |
| arabonate | 0.69 | 0.006 | 1736 | 292.1 |
| N6-carbamoylthreonyladenosine | 0.87 | 0.006 | 2656 | 413 |
| pantothenate (Vitamin B5) | 1.32 | 0.006 | 2218 | 220.1 |
| pyroglutamine | 0.74 | 0.006 | 764 | 129.2 |
| gamma-glutamylmethionine | 0.77 | 0.008 | 1993 | 279.2 |
| X - 16940 | 3.45 | 0.010 | 1694.1 | 204.9 |
| citrulline | 1.21 | 0.010 | 715 | 176.1 |
| tyrosine | 0.86 | 0.010 | 1516 | 182.1 |
| gulono-1,4-lactone | 0.68 | 0.011 | 1862 | 333.1 |
| methylpalmitate (15 or 2) | 1.23 | 0.011 | 5698 | 269.4 |
| X - 16394 | 0.79 | 0.011 | 1719 | 229.2 |
| xylitol | 0.75 | 0.014 | 1677.6 | 217 |
| arginine | 1.15 | 0.015 | 728 | 173.2 |
| 2'-deoxycytidine | 0.84 | 0.021 | 1256 | 228 |
| 2'-O-methylguanosine | 0.59 | 0.022 | 1926 | 298 |
| ophthalmate | 0.47 | 0.023 | 1457 | 290.1 |
| homocitrulline | 0.77 | 0.024 | 832 | 190.1 |
| 5-methylcytidine | 1.13 | 0.025 | 1388 | 258 |
| N-formylmethionine | 0.89 | 0.029 | 1541 | 176.1 |

TABLE 2-continued

Specific Metabolite ratios between small dogs and other dogs.
Correlations with a P value < 0.05 are reported.

| ID | Ratio (Small/Others) | P-Value | Retention Index | Mass |
|---|---|---|---|---|
| bilirubin (E,E) | 0.50 | 0.031 | 4625 | 585.2 |
| X - 17299 | 0.83 | 0.031 | 1265.9 | 229.2 |
| X - 18156 | 0.79 | 0.031 | 1392 | 272.1 |
| palmitoyl sphingomyelin | 0.84 | 0.032 | 2524 | 311.3 |
| X - 16945 | 1.73 | 0.036 | 3457.9 | 351 |
| cysteine-glutathione disulfide | 0.81 | 0.038 | 821 | 427.1 |
| 4-vinylphenol sulfate | 1.29 | 0.040 | 3323 | 199.1 |
| erythritol | 0.87 | 0.040 | 1517.5 | 217 |
| dihomolinolenate (20:3n3 or 3n6) | 1.19 | 0.043 | 5600 | 305.4 |
| anthranilate | 1.36 | 0.049 | 3213 | 138.1 |
| lysine | 0.75 | 0.049 | 1836.7 | 317.2 |
| threitol | 0.86 | 0.049 | 1513 | 217.1 |
| threonate | 0.74 | 0.049 | 1560.7 | 292.1 |

TABLE 3

Clinical measures with P value < 0.05 between small and others
(except for serum T4 in which the data was used for T3/T4 ratio.

| Clinical Measure | Mean small | SEM Small | Mean Others | SEM Others | P value |
|---|---|---|---|---|---|
| Bone Density (gm/cm$^2$) | 0.65 | 0.01 | 0.78 | 0.01 | 3.07E-10 |
| Serum Creatinine (mg/dL) | 0.64 | 0.02 | 0.86 | 0.02 | 7.80E-07 |
| Serum Creatine Kinase (IU/L) | 263.88 | 33.51 | 154.04 | 21.37 | 5.04E-05 |
| Serum Potassium (mmol/L) | 4.31 | 0.05 | 4.65 | 0.05 | 9.33E-04 |
| Serum Total Bilirubin (mg/dL) | 0.10 | 0.01 | 0.13 | 0.01 | 0.02 |
| Serum Aspartate Transaminase (U/L) | 35.68 | 1.99 | 27.91 | 1.07 | 0.02 |
| Serum Gamma-Glutamyltransferase (g/dL) | 6.93 | 0.43 | 5.94 | 0.36 | 0.02 |
| Serum Total Antioxidant Status (mmol/L) | 1.49 | 0.03 | 1.60 | 0.02 | 0.03 |
| Serum T3 (nmol/L) | 1.06 | 0.04 | 0.94 | 0.03 | 0.04 |
| Serum T4 (ug/dL) | 1.68 | 0.19 | 1.77 | 0.09 | 0.27 |
| Serum T3/T4 ((ng/dL)/(ug/dL)) | 54.11 | 4.58 | 40.54 | 4.52 | 0.04 |
| Protein Digestibility (percentage) | 88.00 | 0.38 | 86.00 | 0.57 | 0.01 |

The present data provides metabolic differences identified for small breed dogs based on the results of metabolic profile, blood chemistry, and body composition analysis. The overall antioxidant status in small breed dogs as assessed by many factors was reduced compared to non-small breed dogs, thus they require more dietary antioxidants. It was discovered that small breed dogs also require increased daily intakes of some amino acids, mainly phenylalanine, tyrosine, and lysine; while requiring a lower dietary amount of arginine. Small breed dogs also require greater caloric intake per unit body weight per day to meet their energy needs, i.e. higher metabolic rate. Thus, small breed dogs need increased dietary B vitamins, with the exception of Vitamin B5) to help support the increased metabolic rate. Small breed dogs were also found to have lower bone mineral density, and need increased dietary nutrients to help support bone integrity. Based on these discoveries, the compositions and methods include specific components tailored to small dogs.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A pet food composition for a small dog, the pet food composition comprising:
   protein, fat, carbohydrates, a preservative, and fiber;
   at least three antioxidants selected from the group consisting of: vitamin E in an amount from about 13 IU to about 1,000 IU per 1,000 kcal of metabolizable energy (ME), vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 mg to about 100 mg per kg of the pet food, proanthocyanidins in an amount of about 1 mg to about 100 mg per kg of the pet food, bioflavonoids in an amount of about 1 mg to about 100 mg per kg of the pet food, and catechins in an amount of about 1 mg to about 100 mg per kg of the pet food;
   amino acids including phenylalanine, tyrosine, or the combination of phenylalanine and tyrosine, in an amount of about 1.9 g to about 20 g per 1,000 kcal ME; and lysine in an amount of about 1.6 g to about 20 g per 1,000 kcal ME;
   at least three metabolism components selected from the group consisting of: vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, and vitamin B12 in an amount of about 0.007 mg to about 1.5 mg per 1,000 kcal ME; and
   bone health components including calcium in an amount of about 1.25 g to about 6.25 g per 1,000 kcal ME, phosphorus in an amount of about 1.0 g to about 4.0 g per 1,000 kcal ME, a ratio of calcium to phosphorus ranging from about 1:1 to about 2:1 by weight, magnesium in an amount of about 0.15 g to about 0.55 g per 1,000 kcal ME, and vitamin D in an amount of about 125 IU to about 1,430 IU per 1,000 kcal ME;
   wherein the pet food composition provides about 3,500 to about 6,000 kcal ME per kg of the pet food composition on a dry matter basis.

2. The pet food composition of claim 1, wherein the composition includes each one of vitamin E in an amount from about 13 IU to about 1,000 IU per 1,000 kcal ME, vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 to about 100 mg per kg of the pet food, proanthocyanidins in an amount of about 1 mg to about 100 mg per kg of the pet food, bioflavonoids in an amount of about 1 mg to about 100 mg per kg of the pet food, and catechins in an amount of about 1 mg to about 100 mg per kg of the pet food.

3. The pet food composition of claim 1, wherein the composition includes each one of vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, and vitamin B12 in an amount of about 0.007 mg to about 1.5 mg per 1,000 kcal ME.

4. The pet food composition of claim 1, wherein the vitamin E is in an amount from about 50 IU to about 600 IU per 1,000 kcal ME, the vitamin C is in an amount from about 50 IU to about 600 IU per 1,000 kcal ME, the vitamin A is in an amount of about 6,000 IU to about 50,000 IU per 1,000 kcal ME, the selenium is in an amount of about 0.14 mg to about 0.28 mg per 1,000 kcal ME, the lycopene is in an amount of about 40 mg to about 60 mg per kg of the pet food, the carotenoids are in an amount of about 40 mg to about 60 mg per kg of the pet food, the proanthocyanidins are in an amount of about 1 mg to about 50 mg per kg of the pet food, the bioflavonoids are in an amount of about 1 mg to about 50 mg per kg of the pet food, and the catechins are in an amount of about 1 mg to about 50 mg per kg of the pet food;
the phenylalanine, the tyrosine, or the combination of the phenylalanine and the tyrosine are in an amount of about 4 g to about 12 g per 1,000 kcal ME; and the lysine is in an amount of about 3 g to about 6.5 g per 1,000 kcal ME;
the vitamin B1 is in an amount of about 3.0 mg to about 46.5 mg per 1,000 kcal ME, the vitamin B2 is in an amount of about 1.5 mg to about 10.0 mg per 1,000 kcal ME, the vitamin B3 is in an amount of about 20.0 mg to about 250.0 mg per 1,000 kcal ME, the vitamin B5 is in an amount of about 5.5 mg to about 80.0 mg per 1,000 kcal ME, the vitamin B6 is in an amount of about 3.0 mg to about 35.0 mg per 1,000 kcal ME, the vitamin B7 is in an amount of about 0.035 mg to about 0.8 mg per 1,000 kcal ME, the vitamin B9 is in an amount of about 0.30 mg to about 4.5 mg per 1,000 kcal ME, and the vitamin B12 is in an amount of about 0.015 mg to about 0.3 mg per 1,000 kcal ME; and
the calcium is in an amount of about 2.5 g to about 4.5 g per 1,000 kcal ME, the phosphorus is in an amount of about 2.3 g to about 3.4 g per 1,000 kcal ME, the ratio of calcium to phosphorus ranges from about 1:1 to about 1.6:1 by weight, the magnesium is in an amount of about 0.17 g to about 0.35 g per 1,000 kcal ME, and the vitamin D is in an amount of about 350 IU to about 1,100 IU per 1,000 kcal ME.

5. The pet food composition of claim 1, wherein the pet food includes at least three metabolites for modulating antioxidant concentration in the small dog, the metabolites selected from the group consisting of 5-oxoproline, gamma-glutamylphenylalanine, urate, gamma-glutamylisoleucine, gamma-glutamylleucine, gamma-glutamylvaline, gamma-glutamyltyrosine, xylonate, arabonate, gamma-glutamylmethionine, gulono-1,4-lactone, bilirubin (E,E), cysteine-glutathione disulfide, and threonate.

6. The pet food composition of claim 1, wherein the pet food composition includes at least 3 metabolites for modulating amino acid concentration in the small dog, the metabolites selected from the group consisting of phenylalanine, p-cresol sulfate, phenol sulfate, glutamine, tyrosine, arginine, and lysine.

7. A method of maintaining the health of a small dog, the method comprising administering to the small dog a pet food composition comprising:
protein, fat, carbohydrates, and fiber;
at least three antioxidants selected from the group consisting of: vitamin E in an amount from about 13 IU to about 1,000 IU per 1,000 kcal of metabolizable energy (ME), vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 mg to about 100 mg per kg of the pet food, proanthocyanidins in an amount of about 1 mg to about 100 mg per kg of the pet food, bioflavonoids in an amount of about 1 mg to about 100 mg per kg of the pet food, and catechins in an amount of about 1 mg to about 100 mg per kg of the pet food;
amino acids including phenylalanine, tyrosine, or the combination of phenylalanine and tyrosine in an amount of about 1.9 g to about 20 g per 1,000 kcal ME; and lysine in an amount of about 1.6 g to about 20 g per 1,000 kcal ME;
at least three metabolism components selected from the group consisting of: vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, and vitamin B12 in an amount of about 0.007 mg to about 1.5 mg per 1,000 kcal ME; and
bone health components including calcium in an amount of about 1.25 g to about 6.25 g per 1,000 kcal ME, phosphorus in an amount of about 1.0 g to about 4.0 g per 1,000 kcal ME, a ratio of calcium to phosphorus ranging from about 1:1 to about 2:1 by weight, magnesium in an amount of about 0.15 g to about 0.55 g per 1,000 kcal ME, and vitamin D in an amount of about 125 IU to about 1,430 IU per 1,000 kcal ME;
wherein the pet food composition provides about 3,500 to about 6,000 kcal ME per kg of the pet food composition on a dry matter basis.

8. The method of claim 7, wherein the administering is a regular administration.

9. The method of claim 7, wherein the composition includes each one of vitamin E in an amount from about 13 IU to about 1,000 IU per 1,000 kcal ME, vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 to about 100 mg per kg of the pet food, proanthocyanidins in an amount of about 1 mg to about 100 mg per kg of the pet food, bioflavonoids in an amount of about 1 mg to about 100 mg per kg of the pet food, catechins in an amount of about 1 mg to about 100 mg per kg of the pet food.

10. The method of claim 7, wherein the composition includes each one of vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, vitamin B12 in an amount of about 0.007 mg to about 1.5 mg per 1,000 kcal ME.

11. The method of claim 7, wherein the vitamin E is in an amount from about 50 IU to about 600 IU per 1,000 kcal ME, the vitamin C is in an amount from about 50 IU to about 600 IU per 1,000 kcal ME, the vitamin A is in an amount of about 6,000 IU to about 50,000 IU per 1,000 kcal ME, the selenium is in an amount of about 0.14 mg to about 0.28 mg per 1,000 kcal ME, the lycopene is in an amount of about 40 mg to about 60 mg per kg of the pet food, the carotenoids are in an amount of about 40 mg to about 60 mg per kg of the pet food, the proanthocyanidins are in an amount of about 1 mg to about 50 mg per kg of the pet food, the bioflavonoids are in an amount of about 1 mg to about 50 mg per kg of the pet food, the catechins are in an amount of about 1 mg to about 50 mg per kg of the pet food;
  the phenylalanine, the tyrosine, or the combination of the phenylalanine and the tyrosine are in an amount of about 4 g to about 12 g per 1,000 kcal ME; and the lysine is in an amount of about 3 g to about 6.5 g per 1,000 kcal ME;
  the vitamin B1 is in an amount of about 3.0 mg to about 46.5 mg per 1,000 kcal ME, the vitamin B2 is in an amount of about 1.5 mg to about 10.0 mg per 1,000 kcal ME, the vitamin B3 is in an amount of about 20.0 mg to about 250.0 mg per 1,000 kcal ME, the vitamin B5 is in an amount of about 5.5 mg to about 80.0 mg per 1,000 kcal ME, the vitamin B6 is in an amount of about 3.0 mg to about 35.0 mg per 1,000 kcal ME, the vitamin B7 is in an amount of about 0.035 mg to about 0.8 mg per 1,000 kcal ME, the vitamin B9 is in an amount of about 0.30 mg to about 4.5 mg per 1,000 kcal ME, the vitamin B12 is in an amount of about 0.015 mg to about 0.3 mg per 1,000 kcal ME; and
  the calcium is in an amount of about 2.5 g to about 4.5 g per 1,000 kcal ME, the phosphorus is in an amount of about 2.3 g to about 3.4 g per 1,000 kcal ME, the ratio of calcium to phosphorus ranges from about 1:1 to about 1.6:1 by weight, the magnesium is in an amount of about 0.17 g to about 0.35 g per 1,000 kcal ME, and the vitamin D is in an amount of about 350 IU to about 1,100 IU per 1,000 kcal ME.

12. The method of claim 7, wherein the pet food includes at least three metabolites for modulating antioxidant concentration in the small dog, the metabolites selected from the group consisting of 5-oxoproline, gamma-glutamylphenylalanine, urate, gamma-glutamylisoleucine, gamma-glutamylleucine, gamma-glutamylvaline, gamma-glutamyltyrosine, xylonate, arabonate, gamma-glutamylmethionine, gulono-1,4-lactone, bilirubin (E,E), cysteine-glutathione disulfide, and threonate.

13. The method of claim 7, wherein the pet food composition includes at least 3 metabolites for modulating amino acid concentration in the small dog, the metabolites selected from the group consisting of phenylalanine, p-cresol sulfate, phenol sulfate, glutamine, tyrosine, arginine, and lysine.

14. A method of modulating at least one health parameter selected from the group consisting of bone density, fecal quality, and serum total antioxidant status, the method comprising administering to a small dog a pet food composition comprising:
  protein, fat, carbohydrates, and fiber;
  at least three antioxidants selected from the group consisting of: vitamin E in an amount from about 13 IU to about 1,000 IU per 1,000 kcal of metabolizable energy (ME), vitamin C in an amount from about 0.25 IU to about 1,000 IU per 1,000 kcal ME, vitamin A in an amount of about 1,300 IU to about 62,500 IU per 1,000 kcal ME, selenium in an amount of about 0.1 mg to about 0.5 mg per 1,000 kcal ME, lycopene in an amount of about 1 mg to about 100 mg per kg of the pet food, carotenoids in an amount of about 1 mg to about 100 mg per kg of the pet food, proanthocyanidins in an amount of about 1 mg to about 100 mg per kg of the pet food, bioflavonoids in an amount of about 1 mg to about 100 mg per kg of the pet food, and catechins in an amount of about 1 mg to about 100 mg per kg of the pet food;
  amino acids including phenylalanine, tyrosine, or the combination of phenylalanine and tyrosine in an amount of about 1.9 g to about 20 g per 1,000 kcal ME; and lysine in an amount of about 1.6 g to about 20 g per 1,000 kcal ME;
  at least three metabolism components selected from the group consisting of: vitamin B1 in an amount of about 0.56 mg to about 150.0 mg per 1,000 kcal ME, vitamin B2 in an amount of about 1.3 mg to about 50.0 mg per 1,000 kcal ME, vitamin B3 in an amount of about 3.4 mg to about 500.0 mg per 1,000 kcal ME, vitamin B5 in an amount of about 3.0 mg to about 300.0 mg per 1,000 kcal ME, vitamin B6 in an amount of about 0.38 mg to about 200.0 mg per 1,000 kcal ME, vitamin B7 in an amount of about 0.01 mg to about 10.0 mg per 1,000 kcal ME, vitamin B9 in an amount of about 0.054 mg to about 40.0 mg per 1,000 kcal ME, and vitamin B12 in an amount of about 0.007 mg to about 1.5 mg per 1,000 kcal ME; and
  bone health components including calcium in an amount of about 1.25 g to about 6.25 g per 1,000 kcal ME, phosphorus in an amount of about 1.0 g to about 4.0 g per 1,000 kcal ME, a ratio of calcium to phosphorus ranging from about 1:1 to about 2:1 by weight, magnesium in an amount of about 0.15 g to about 0.55 g per 1,000 kcal ME, and vitamin D in an amount of about 125 IU to about 1,430 IU per 1,000 kcal ME;
  wherein the pet food composition provides about 3,500 to about 6,000 kcal ME per kg of the pet food composition on a dry matter basis.

15. The method of claim 14, wherein, after regular administration of the pet food to the small dog, bone density or serum total antioxidant status is increased or decreased by at least 5%, or fecal quality is improved.

* * * * *